United States Patent [19]
Okamoto et al.

[11] Patent Number: 5,886,220
[45] Date of Patent: Mar. 23, 1999

[54] PROCESS FOR PREVENTING POLYMERIZATION OF VINYL COMPOUND

[75] Inventors: Kenji Okamoto; Takashi Nakagawa; Hideaki Mimaki; Kouji Tomita, all of Tokuyama, Japan

[73] Assignee: Idemitsu Petrochemical Co., Ltd., Tokyo, Japan

[21] Appl. No.: 793,600
[22] PCT Filed: Aug. 29, 1995
[86] PCT No.: PCT/JP95/01705
  § 371 Date: Mar. 5, 1997
  § 102(e) Date: Mar. 5, 1997
[87] PCT Pub. No.: WO96/07631
  PCT Pub. Date: Mar. 14, 1996

[30] Foreign Application Priority Data

Sep. 9, 1994 [JP] Japan ................... 6-215705

[51] Int. Cl.[6] ............ C07C 57/04; C07C 57/02
[52] U.S. Cl. .................... 562/598; 562/599
[58] Field of Search .................... 562/599, 598

[56] References Cited

U.S. PATENT DOCUMENTS

| | | | |
|---|---|---|---|
| 4,021,310 | 5/1977 | Shimizu et al. | 203/8 |
| 4,532,011 | 7/1985 | Colvin | 203/9 |
| 5,128,484 | 7/1992 | Kita et al. | 548/549 |
| 5,130,471 | 7/1992 | Heiman et al. | 560/205 |
| 5,177,164 | 1/1993 | De Vries et al. | 526/82 |
| 5,322,960 | 6/1994 | Sakamoto et al. | 560/205 |
| 5,371,280 | 12/1994 | Haramaki et al. | 562/26 |

FOREIGN PATENT DOCUMENTS

| | | |
|---|---|---|
| 0 155 898 | 9/1985 | European Pat. Off. . |
| 0 485 169 | 5/1992 | European Pat. Off. . |

OTHER PUBLICATIONS

Lewis, Hawley's Condensed Chemical Dictionary, 12th edition, p. 908, 1993.

*Primary Examiner*—Gary Geist
*Assistant Examiner*—Rosalynd Keys
*Attorney, Agent, or Firm*—Oblon, Spivak, McClelland, Maier & Neustadt, P.C.

[57] ABSTRACT

There is disclosed a process for preventing the polymerization of a vinyl compound which comprises allowing water in an amount of 0.05 to 5% by weight based on the vinyl compound or a corrosion inhibitive substance selected from an alcohol, an inorganic acid or its salt, an aromatic carboxylic acid or its salt and a zinc-containing salt in an amount of preferably 0.01 to 5% by weight based on the same, to coexist with a metallic salt of dithiocarbamic acid, in preventing the polymerization of the vinyl compound with the metallic salt of dithiocarbamic acid. The above process makes it possible to effectively inhibit the polymerization of acrylic acid, methacrylic acid, etc. in the distillation system, etc. of the production process for the above acids as well as the corrosion of the equipment and machinery to be used therein and also to assure long-term stable continuous operation of the equipment and machinery.

3 Claims, No Drawings

PROCESS FOR PREVENTING POLYMERIZATION OF VINYL COMPOUND

TECHNICAL FIELD

The present invention relates to a process for preventing the polymerization of a vinyl compound. More particularly, it pertains to a process for preventing the polymerization of a vinyl compound which process is capable of effectively inhibiting the polymerization of acrylic acid, methacrylic acid or the like in the distillation system, etc. of the production process for the above-mentioned acid, etc. as well as the corrosion of the equipment and machinery to be used therein and at the same time, enables long-term stable continuous operation of the equipment and machinery.

BACKGROUND ART

It has heretofore been known that a vinyl compound such as styrene, acrylic acid, methacrylic acid, an acrylic ester, a methacrylic ester and acrylonitrile has the property of liability to polymerization by light, heat or the like. In the production process of the above-mentioned vinyl compound, various distillation operations are put into practice for the purpose of separating, recovering, concentrating or purifying the objective vinyl compound. However, the aforesaid vinyl compound is apt to bring about an unfavorable situation such as various troubles in the distillation step which finally make it impossible to proceed with a long-term stable continuous operation, since as mentioned above, the compound is liable to polymerization by light, heat or the like to form a polymer-like substance.

In order to avoid such a situation, there has heretofore been adopted a process in which the distillation operations are put into practice in the presence of a polymerization inhibitor, which is exemplified by hydroquinone, methoquinone (p-methoxyphenol), p-tert-butyl catechol, tert-butylhydroquinone and phenothiazine. Nevertheless, the actual situation is that any of the above-mentioned polymerization inhibitors does not necessarily exert sufficient effect on acrylic acid, methacrylic acid and the like because of their extreme liability to polymerization.

Aside from the foregoing, it is known that cupric dibutyldithiocarbamate is a substance which is capable of extremely effectively preventing the polymerization in liquid phase of acrylic acid, methacrylic acid, etc., but it has been difficult to employ the substance in an industrial manufacturing plant because of its fatal disadvantage that it corrodes an equipment made of, for example, SUS 316.

On the other hand, there is proposed a method in which a manganate is employed as a corrosion inhibitor in combination with a metallic salt of dithiocarbamic acid. (Refer to Japanese Patent Application Laid-Open No. 51403/1993). However, the aforesaid method is not satisfactory because of its insufficient corrosion inhibition effect.

DISCLOSURE OF THE INVENTION

It is an object of the present invention to provide, under such circumstances, a process for preventing the polymerization of a vinyl compound which process is capable of efficiently inhibiting the polymerization of a vinyl compound, especially acrylic acid, methacrylic acid or the like in the distillation system, etc. of the production process for the above-mentioned acid, as well as the corrosion of the equipment and machinery to be used therein, and at the same time, enables long-term stable continuous operation of the equipment and machinery.

As a result of intensive research and investigation accumulated by the present inventors in order to attain the above-mentioned object, it has been found that the object can be attained by paying attention to the excellent corrosion inhibition effect of a metallic salt of dithiocarbamic acid typified by cupric dibutyldithiocarbamate and making use thereof in combination with a specific corrosion inhibitive substance typified by water. The present invention has been accomplished by the foregoing finding and information.

Specifically, the present invention provides a process for preventing the polymerization of a vinyl compound which comprises allowing water in an amount of 0.05 to 5% by weight based on the vinyl compound to coexist with a metallic salt of dithiocarbamic acid, in preventing the polymerization of the vinyl compound with the metallic salt of dithiocarbamic acid in the production process of the vinyl compound.

The present invention further provides a process for preventing the polymerization of a vinyl compound which comprises allowing at least one corrosion inhibitive substance selected from the group consisting of (a) an alcohol, (b) an inorganic acid or a salt thereof, (c) an aromatic carboxylic acid or a salt thereof and (d) a zinc-containing salt to coexist with a metallic salt of dithiocarbamic acid, in preventing the polymerization of the vinyl compound with the metallic salt of dithiocarbamic acid in the production process of the vinyl compound.

THE MOST PREFERRED EMBODIMENT TO CARRY OUT THE INVENTION

As the vinyl compound to which the process of the present invention is applicable, mention may be made of, for example, styrene, acrylic acid, methacrylic acid, an acrylic ester, a methacrylic ester and acrylonitrile, of which acrylic acid and methacrylic acid are particularly preferable.

There is used in the process according to the present invention, a metallic salt of dithiocarbamic acid as a polymerization inhibitor for the above-mentioned vinyl compound. As the metallic salt of dithiocarbamic acid usable therein, mention may be made of the compound having the structure repersented by the general formula (I)

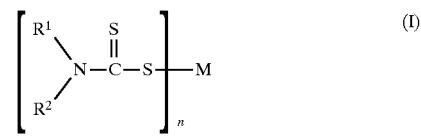

wherein $R^1$ and $R^2$ may be the same as or different from each other and are each a phenyl group or an alkyl group which has 1 to 8 carbon atoms, may be straight-chain or branched and are specifically exemplified by methyl group, ethyl group, propyl group, butyl group, pentyl group and hexyl group; M stands for a metal such as nickel, zinc, copper, iron and a transition metal (Mn, Co, etc.); and n is the valency of the metal M.

Examples of the metallic salt of dithiocarbamic acid represented by the general formula (I) include cupric dimethyldithiocarbamate, cupric diethyldithiocarbamate, cupric dipropyldithiocarbamate, cupric dibutyldithiocarbamate, cupric dipentyldithiocarbamate, cupric dihexyldithiocarbamate, cupric diphenyldithiocarbamate, cupric methylethyldithiocarbamate, cupric methylpropyldithiocarbamate, cupric methylbutyldithiocarbamate, cupric methylpentyldithiocarbamate, cupric

| | |
|---|---|
| methylhexyldithiocarbamate, | cupric |
| methylphenyldithiocarbamate, | cupric |
| ethylpropyldithiocarbamate, | cupric |
| ethylbutyldithiocarbamate, | cupric |
| ethylpentyldithiocarbamate, | cupric |
| ethylhexyldithiocarbamate, | cupric |
| ethylphenyldithiocarbamate, | cupric |
| propylbutyldithiocarbamate, | cupric |
| propylpentyldithiocarbamate, | cupric |
| propylhexyldithiocarbamate, | cupric |
| propylphenyldithiocarbamate, | cupric |
| butylpentyldithiocarbamate, | cupric |
| butylhexyldithiocarbamate, | cupric |
| butylphenyldithiocarbamate, | cupric |
| pentylhexyldithiocarbamate, | cupric | pentylphenyldithiocarbamate, cupric hexylphenyldithiocarbamate and a nickel salt, a zinc salt, an iron salt an a transition-metal salt (Mn, Co, etc.) each corresponding to the cupric salt exemplified above. Of the above-exemplified metallic salts of dithiocarbamic acid, cupric dithiocarbamate is preferable and cupric dibutyldithiocarbamate is particularly preferable.

The aforesaid metallic salt of dithiocarbamic acid as a polymerization inhibitor may be used alone or in combination with at least one other metallic salt. The amount thereof to be added to the vinyl compound is usually selected in the range of 0.01 to 1, preferable 0.05 to 0.5% by weight based on the vinyl compound. An amount thereof less than 0.01% by weight can not sufficiently exhibit the polymerization inhibition effect, whereas that more than 1% by weight can not enhance the effect in proportion to the amount of the inhibitor added, thus causing disadvantage from the economical point of view.

In order to inhibit the corrosion of the equipment and machinery in the process according to the present invention water may be allowed to coexist with the above-mentioned metallic salt of dithiocarbamic acid. It is necessary in this case to regulate the amount of the coexisting water to the range of 0.05 to 5% by weight based on the vinyl compound. The amount of water less than 0.05% by weight can not sufficiently exhibit the corrosion inhibition effect, whereas that more than 5% by weight requires excessively large amount of energy to separate water, thereby causing disadvantage from the economical point of view. An amount of water preferable from both the viewpoints of corrosion inhibition effect and economical efficiency is in the range of 0.07 to 0.5% by weight based on the vinyl compound.

Moreover in order to inhibit the corrosion of the equipment and machinery in the process according to the present invention, there may be used a corrosion inhibitive substance comprising at least one member selected from the group consisting of (a) an alcohol, (b) an inorganic acid or a salt thereof, (c) an aromatic carboxylic acid or a salt thereof and (d) a zinc-containing salt.

As the alcohol to be used as the component (a) in the corrosion inhibitive substance, mention may be made of, for example, a primary alcohol having 1 to 10 carbon atoms such as methyl alcohol, ethyl alcohol, n-propyl alcohol, n-butyl alcohol, isobutyl alcohol, n-octyl alcohol and 2-ethylhexyl alcohol, a polyhydric alcohol such as ethylene glycol; propylene glycol; 1,4-butane diol; and 1,6-hexane diol, and an aromatic alcohol such as phenol, cresol, xylenol, benzyl alcohol and phenethyl alcohol. Of these a polyhydric alcohol is preferable. Examples of the preferable inorganic acid to be used as the component (b) include an oxoacid, which is specifically exemplified by boric acid, phosphoric acid, nitric acid and sulfuric acid. Of these phosphoric acid is particularly preferable. Examples of the salt of the inorganic acid include a nickel salt, a zinc salt, a copper salt, an iron salt and a salt of any of various transition metals (Mn, Co, etc.)

Examples of the aromatic carboxylic acid to be used as the component (c) and a salt thereof include benzoic acid, naphthalenecarboxylic acid, salicylic acid, p-hydroxybenzoic acid, oxynaphthoic acid, and a nickel salt, a zinc salt, a copper salt, an iron salt and any of various transition metals (Mn, Co, etc.) each of the aforesaid aromatic carboxylic acid. Examples of the zinc-containing salt to be used as the component (d) include zinc formate, zinc acetate and zinc dithiocarbamate.

The above-exemplified corrosion inhibitive substances may be use alone or in combination. The amount thereof to be used is preferably in the range of 0.001 to 5% by weight based on the vinyl compound. An amount thereof less than 0.001% by weight can not sufficiently exhibit the corrosion inhibition effect, whereas that more than 5% by weight can not enhance the effect in proportion to the amount of the inhibitor added, causing a fear of other disadvantage. In order to effectively carry out corrosion inhibition without causing any other disadvantage, the amount of the corrosion inhibitive substance to be used is preferably in the range of 0.01 to 3% by weight, particularly preferably 0.1 to 1% by weight based on the vinyl compound.

In the case where an oxoacid, especially phosphoric acid among the inorganic acid is used as a corrosion inhibitive substance, the amount of phosphoric acid is preferably at least 0.1 (weight ratio) based on the aforesaid metallic salt of dithiocarbamic acid, especially cupric dithiocarbamate.

In the process according to the present invention, the aforesaid polymerization inhibitor may be incorporated, as desired, with an other known polymerization inhibitor such as hydroquinone, methoquinone, p-tert-butyl catechol, tert-butylhydroquinone and phenothiazine to the extent that the object of the present invention is not impaired thereby.

In the process according to the present invention, the treatment temperature of the vinyl compound containing the above-mentioned metallic salt of dithiocarbamic acid and water, or the metallic salt of dithiocarbamic acid and the corrosion inhibitive substance varies depending upon the type of the vinyl compound, but in the case of acrylic acid or methacrylic acid, it is usually in the range of 50° to 130° C. The polymerization inhibition effect and corrosion inhibition effect are sufficiently exhibited when the treatment temperature is within the aforesaid range.

In the following, the present invention will be described in more detail with reference to the working examples, which however shall not be construed to limit the invention thereto.

COMPARATIVE EXAMPLE 1

A 500 mL (milliliter) separable flask equipped with a reflux tube was charged with a SUS 316-made test piece (40×15×3 mm) which had been subjected to oxidation film treatment and 200 mL of acrylic acid, and the content in the flask was brought into a reflux state, while the flask inside temperature was kept at 110° C. under reduced pressure. Into the flask was continuously fed a solution of cupric dibutylthiocarbamate as polymerization inhibitor in acrylic acid having a water content of 210 ppm by weight, said solution having a concentration of 3500 ppm by weight based on the acrylic acid at a rate of 40 mL/hour, while the solution in the flask was continuously withdrawn at the same rate. As a result, the weight loss of the test piece due to corrosion during a period of 10 days was 0.334 g.

COMPARATIVE EXAMPLE 2

The procedure in Comparative Example 1 was repeated to carry out the experiment on polymerization and corrosion except that phenothiazine was used as a polymerization inhibitor in place of cupric dibutyldithiocarbamate. As a result, any weight loss of a test piece due to corrosion during a period of 10 days was not recognized. It is understood by the comparison between Comparative Examples 1 and 2 that cupric dibutyldithiocarbamate is corrosive.

COMPARATIVE EXAMPLE 3

The procedure in Comparative Example 1 was repeated to carry out the experiment on polymerization and corrosion except that into the flask was fed a solution of manganese acetate at a concentration of 3,630 ppm by weight based on acrylic acid along with the cupric dibutyldithiocarbamate at a concentration same as in Comparative Example 1 in acrylic acid having a water content of 240 ppm by weight. As a result, the weight loss of the test piece due to corrosion during a period of 10 days was 0.080 g.

Examples 1 and 2

The procedure in Comparative Example 1 was repeated to carry out the experiment on polymerization and corrosion except that the water content in the acrylic acid was set at 910 ppm by weight (Example 1) and 1,740 ppm by weight (Example 2) each based on acrylic acid. As a result, the weight loss of the test piece due to corrosion during a period of 10 days was 0.005 g and at most 0.001 g, respectively.

Example 3

The procedure in Comparative Example 1 was repeated to carry out the experiment on polymerization and corrosion except that into the flask was fed a solution of zinc dibutyldithiocarbamate at a concentration of 3,500 ppm by weight based on acrylic acid along with the cupric dibutyldithiocarbamate at a concentration same as in Comparative Example 1 in acrylic acid having a water content of 970 ppm by weight. As a result, the weight loss of the test piece due to corrosion during a period of 10 days was 0.001 g.

Example 4

The procedure in Comparative Example 1 was repeated to carry out the experiment on polymerization and corrosion except that into the flask was fed a solution of ethylene glycol at a concentration of 10,000 ppm by weight based on acrylic acid along with the cupric dibutyldithiocarbamate at a concentration same as in Comparative Example 1 in acrylic acid having a water content of 120 ppm by weight. As a result, the weight loss of the test piece due to corrosion during a period of 10 days was 0.003 g.

Example 5

The procedure in Comparative Example 1 was repeated to carry out the experiment on polymerization and corrosion except that into the flask was fed a solution of zinc phosphate at a concentration of 1,700 ppm by weight based on acrylic acid along with the cupric dibutyldithiocarbamate at a concentration same as in Comparative Example 1 in acrylic acid having a water content of 140 ppm by weight. As a result, the weight loss of the test piece due to corrositon during a period of 10 days was 0.009 g.

Example 6

The procedure in Comparative Example 1 was repeated to carry out the experiment on polymerization and corrosion except that into the flask was fed a solution of phosphoric acid at a concentration of 8,500 ppm by weight based on acrylic acid along with the cupric dibutyldithiocarbamate at a concentration same as in Comparative Example 1 in acrylic acid having a water content of 322 ppm by weight. As a result, the weight loss of the test piece due to corrosion during a period of 10 days was 0.001 g.

Example 7

The procedure in Comparative Example 1 was repeated to carry out the experiment on polymerization and corrosion except that into the flask was fed a solution of boric acid at a concentration of 3,300 ppm by weight based on acrylic acid along with the cupric dibutyldithiocarbamate at a concentration same as in Comparative Example 1 in acrylic acid having a water content of 200 ppm by weight. As a result, the weight loss of the test piece due to corrosion during a period of 10 days was 0.001 g.

Example 8

The procedure in Comparative Example 1 was repeated to carry out the experiment on polymerization and corrosion except that into the flask was fed a solution of benzoic acid at a concentration of 10,000 ppm by weight based on acrylic acid along with the cupric dibutyldithiocarbamate at a concentration same as in Comparative Example 1 in acrylic acid having a water content of 135 ppm by weight. As a result, the weight loss of the test piece due to corrosion during a period of 10 days was 0.002 g.

The results of the above-mentioned comparative examples and examples are collectively given in Table 1.

No polymerirzation of acrylic acid was recognized in any of the Examples 1 to 8 and Comparative Example 1 and 3. However, a sign of polymerization of acrylic acid was recognized in Comparative Example 2.

TABLE 1-1

| | Content, ppm by weight based on acrylic acid | | |
|---|---|---|---|
| | Comparative Example 1 | Comparative Example 2 | Comparative Example 3 |
| Cupric dibutyldithiocarbamate | 3,500 | — | 3,500 |
| Phenothiazine | — | 3,500 | — |
| Corrosion inhibitor (ppm) | | | |
| Water | 210 | 90 | 240 |
| Zinc dibutyldithiocarbamate | — | — | — |
| Ethylene glycol | — | — | — |
| Zinc phosphate | — | — | — |
| Phosphoric acid | — | — | — |
| Boric acid | — | — | — |
| Benzoic acid | — | — | — |
| Manganese acetate | — | — | 3,630 |
| Weight loss of SUS 316-test piece for 10 days (g) | 0.334 | <0.001 | 0.080 |

TABLE 1-2

| | Content, ppm by weight based on acrylic acid | | | |
|---|---|---|---|---|
| | Example 1 | Example 2 | Example 3 | Example 4 |
| Cupric dibutyl-dithiocarbamate | 3,500 | 3,500 | 3,500 | 3,500 |
| Phenothiazine | — | — | — | — |
| Corrosion inhibitor (ppm) | | | | |
| Water | 910 | 1,740 | 970 | 120 |
| Zinc dibutyldithiocarbamate | — | — | 3,500 | — |
| Ethylene glycol | — | — | — | 10,000 |
| Zinc phosphate | — | — | — | — |
| Phosphoric acid | — | — | — | — |
| Boric acid | — | — | — | — |
| Benzoic acid | — | — | — | — |
| Manganese acetate | — | — | — | — |
| Weight loss of SUS 316-test piece for 10 days (g) | 0.005 | <0.001 | 0.001 | 0.003 |

TABLE 1-3

| | Content, ppm by weight based on acrylic acid | | | |
|---|---|---|---|---|
| | Example 5 | Example 6 | Example 7 | Example 8 |
| Cupric dibutyl-dithiocarbamate | 3,500 | 3,500 | 3,500 | 3,500 |
| Phenothiazine | — | — | — | — |
| Corrosion inhibitor (ppm) | | | | |
| Water | 140 | 322 | 200 | 135 |
| Zinc dibutyldithiocarbamate | — | — | — | — |
| Ethylene glycol | — | — | — | — |
| Zinc phosphate | 1,700 | — | — | — |
| Phosphoric acid | — | 8,500 | — | — |
| Boric acid | — | — | 3,300 | — |
| Benzoic acid | — | — | — | 10,000 |
| Manganese acetate | — | — | — | — |
| Weight loss of SUS 316-test piece for 10 days (g) | 0.009 | 0.001 | 0.001 | 0.002 |

Example 9

The procedure in Comparative Example 1 was repeated to carry out the experiment on polymerization and corrosion except that into the flask was fed a solution of phosphoric acid at a concentration of 50 ppm by weight based on acrylic acid along with the cupric dibutyldithiocarbamate at a concentration of 500 ppm by weight based on the same in acrylic acid and that the flask inside temperature was kept at 130° C. instead of 110° C. As a result, the weight loss of the test piece due to corrosion during a period of 10 days was 0.001 g.

Example 10

The procedure in Comparative Example 1 was repeated to carry out the experiment on polymerization and corrosion except that into the flask was fed a solution of phosphoric acid at a concentration of 4,000 ppm by weight based on acrylic acid along with the cupric dibutyldithiocarbamate at a concentration of 15,000 ppm by weight based on the same in acrylic acid and that the flask inside temperature was kept at 130° C. instead of 110° C. As a result, the weight loss of the test piece due to corrosion during a period of 10 days was 0.022 g.

Examples 11 to 21

The procedure in Comparative Example 1 was repeated to carry out the experiment on polymerization and corrosion except that into the flask was fed a solution of phosphoric acid at a concentration shown in Table 2 along with the cupric dibutyldithiocarbamate at a concentration also shown in Table 2 in acrylic acid. As a result, the weight loss of the test piece due to corrosion during a period of 10 days was 0.001 g for each of the examples.

TABLE 2

| | Content of cupric dibutyldithiocarbamate (ppm by weight) based on acrylic acid | Content of phosphoric acid (ppm by weight) based on acrylic acid |
|---|---|---|
| Example 11 | 300 | 100 |
| Example 12 | 300 | 400 |
| Example 13 | 500 | 600 |
| Example 14 | 3500 | 100 |
| Example 15 | 3500 | 400 |
| Example 16 | 3500 | 900 |
| Example 17 | 3500 | 4000 |
| Example 18 | 3500 | 8500 |
| Example 19 | 7000 | 8500 |
| Example 20 | 10000 | 1300 |
| Example 21 | 15000 | 20000 |

INDUSTRIAL APPLICABILITY

As described hereinbefore, according to the present invention, it is made possible to effectively inhibit the polymerization of acrylic acid, methacrylic acid or the like in the distillation system, etc. of the production process for the above-mentioned acid, etc. as well as the corrosion of the equipment and machinery to be used therein and at the same time, to assure long-term stable continuous operation of the equipment and machinery.

We claim:

1. A process for preventing the polymerization of a vinyl compound which comprises allowing water in an amount of 0.05 to 5% by weight based on the vinyl compound to coexist with a metallic salt of dithiocarbamic acid, in preventing the polymerization of the vinyl compound with the metallic salt of dithiocarbamic acid in the production process of the vinyl compound.

2. The process according to claim 1 wherein the vinyl compound is acrylic acid or methacrylic acid.

3. The process according to claim 1 wherein the metallic salt of dithiocarbamic acid is cupric dibutyldithiocarbamate.

* * * * *